(12) United States Patent
Schneider

(10) Patent No.: US 7,414,034 B2
(45) Date of Patent: Aug. 19, 2008

(54) TREATMENT OF PARKINSON'S DISEASE WITH OLIGONUCLEOTIDES

(75) Inventor: Jay S. Schneider, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 293 days.

(21) Appl. No.: 10/937,824

(22) Filed: Sep. 9, 2004

(65) Prior Publication Data

US 2005/0020530 A1    Jan. 27, 2005

Related U.S. Application Data

(63) Continuation of application No. 09/435,249, filed on Nov. 5, 1999, now abandoned.

(60) Provisional application No. 60/107,191, filed on Nov. 5, 1998.

(51) Int. Cl.
*A01N 43/04* (2006.01)
*A61K 31/70* (2006.01)
*C07H 21/02* (2006.01)
*C07H 21/04* (2006.01)

(52) U.S. Cl. .................. 514/44; 536/23.1; 536/24.3; 536/24.33; 536/24.5

(58) Field of Classification Search .............. 514/44
See application file for complete search history.

(56) References Cited

U.S. PATENT DOCUMENTS 5,929,042 A    7/1999   Troy et al. .................. 514/44
5,929,226 A    7/1999   Padmapriya et al. ....... 536/25.3

OTHER PUBLICATIONS

Braasch et al. Novel Antisense and Peptide Nucleic Acid Strategies for Controlling Gene Expression. Biochemistry, 2002 vol. 41:4503-4510.*
Tamm, I. et al. Antisense therapy in oncology: new hope for an old idea. The Lancet. Aug. 2001, 358: 489-497.*
Ma et al., *Biotechnology Annual Review*, vol. 5, 2000, pp. 155-196.
Jen at al., *Stem Cells*, vol. 18, 2000, pp. 307-319.
Green et al., *J. Am. Coll. Surg.*, vol. 191, No. 1, Jul. 2000, pp. 93-105.

(Continued)

*Primary Examiner*—Sean McGarry
*Assistant Examiner*—Terra Cotta Gibbs
(74) *Attorney, Agent, or Firm*—Pepper Hamilton, LLP

(57) ABSTRACT

The present invention relates to a method of treatment of Parkinson's disease, and to the use of antisense oligonucleotides or triplex oligonucleotides introduced into targeted brain structures to decrease the function of brain circuits known to be overactive in the Parkinsonian brain. Antisense or triplex oligonucleotides are targeted to the internal globus pallidus and/or substantia nigra pars reticulata (SNr) where the expression of glutamic acid decarboxylase ($GAD_{67}$, $GAD_{65}$, or a combination of the two isoforms) is downregulated. The present invention also relates to a method of treatment of Parkinson's disease where antisense or triplex oligonucleotides are targeted to the internal globus pallidus and/or substantia nigra pars reticulata for the downregulation of glutamate receptors. The present invention further relates to a method of treatment of Parkinson's disease where antisense or triplex oligonucleotides are targeted to the thalamic motor nuclei for the downregulation of GABA receptors.

24 Claims, 7 Drawing Sheets

OTHER PUBLICATIONS

Agrawal et al., *Molecular Medicine Today*, vol. 6, Feb. 2000, pp. 72-81.

Bennett et al., *Chapter 2 from Methods in Molecular Medicine: Antisense Therapeutics* (Ed. Agrawal), Humana. Press Inc. Totowa, N.J., 1996, pp. 13-46.

Branch, *TIBS* 23, pp. 45-50, Feb. 1998.

Flanagan et al., *Nature Biotechnology*, vol. 17, No. 1, pp. 48-52, Jan. 1999.

McCarthy, M.M. et al., "Intracerebral administration of antisense oligodeoxynucleotides to GAD 65 and GAD 67 mRNAs modulate reproductive behavior in the famale rat", *Brain Research*, 1994, 636, 209-220.

Mitsushima, D. et al., "Role of glutamic acid decarboxylase in the prepubertal inhibition of the luteinizing hormone releasing hormone release in female rhesus monkeys", *The Journal of Neuroscience*, 1996, 16(8), 2563-2573.

Stull, R.A. et al., "Predicting Antisense Oligonucleotide Inhibitory Efficacy: A Computational Approach Using Histograms and Thermodynamic Indices", *Nucleic Acids Research*, vol. 20, No. 13, pp. 3501-3508, 1992.

Stull, R.A., et al., "An in vitro Messenger RNA Binding Assay as a Tool for Identifying Hybridization-competent Antisense Oligonucleotides", *Antisense & Nucleic Acid Drug Development*, vol. 6, pp. 221-228, 1996.

Bacon, Thomas A. and Wickstrom, E., "Walking Along Human c-*myc* mRNA with Antisense Oligodeoxynucleotides: Maximum Efficacy at the 5' Cap Region", *Oncogene Research*, vol. 6., pp. 13-19, 1991.

Bennett, C.F. et al., "Pharmacology of Antisense Therapeutic Agents", *Methods in Molecular Medicine: Antisense Therapeutics* (Agrawal, S., ed.), Humana Press, Totowa, New Jersey, pp. 13-46, 1996.

Akhtar, S. and Agrawal, S., "In vivo Studies with Antisense Oligonucleotides", *Trends in Pharmacol. Sciences*, vol. 18, pp. 12-18, 1997.

Brysch, et al., "Antisense-Mediated Inhibition of Protein Synthesis", *Methods in Molecular Medicine: Antisense Therapeutics*, (Agrawal, S., ed.), Humana Press, Totowa, New Jersey, pp. 166 and 175-176, 1996.

Cossum, P.A. et al., "Disposition of the C-Labeled Phosphorothioate Oligonucleotide, ISIS 2105, after Intravenous Administration to Rats", *J. Pharmacol. Exp. Ther.*, vol. 267, No. 3, pp. 1181-1190, 1993.

Cossum, P.A., et al., "Pharmacokinetics of a C-Labeled Phosphorothioate Oligonucleotide, ISIS 2105, after Intradermal Administration to Rats", *J. Pharmacol. Exp. Ther.*, vol. 269, No. 1, pp. 89-94, 1994.

Agrawal, S., et al., "Pharmacokinetics, Biodistribution, and Stability of Oligodeoxynucleotide Phophorothioates in Mice", *Proc. Natl. Acad. Sci.*, vol. 88, pp. 7595-7599, 1991.

Temsamani, J., et al., "Pharmacokinetics, Biodistribution , and Stability of Capped Oligodeoxynucleotide Phosphorothioates in Mice", *Antisense Res. Dev.*, vol. 3: 277-284, 1993.

Sands, H., et al., "Biodistribution and Metabolism of Internally H-Labeled Oligonucleotides. I. Comparison of a Phosphodiester and a Phosphorothioate", *Mol. Pharmacol.*, vol. 45, pp. 932-943, 1994.

Saijo, Y., et al., "Pharmacokinetics, Tissue Distribution , and Stability of Antisense Oligodeoxynucleotide Phosphorothiate ISIS 3466 in Mice", *Oncol. Res.*, vol. 6:243-249, 1994.

DeDiesbach, P., et al., "Identification, Purification and Partial Characterization of an Oligonucleotide Receptor in Membranes of HepG2 Cells", Nucleic Acids Res Feb. 15, 2000;28(4):868-74.

Loke, S.L., et al., "Characterization of Oligonucleotide Transport into Living Cells", *Proc. Natl. Acad. Sci.* USA, vol. 86, pp. 3474-3478, May 1989.

Hanss, B., et al., "Identification and Characterization of a Cell Membrane Nucleic Acid Channel", *Proc. Natl. Acad. Sci.* USA, vol. 95, pp. 1921-1926, Feb. 1998.

Benimetskaya, L. et al., "Mac-1 (CD11b/CD18) is an Oligodeoxynucleotide-binding Protein", *Nature Medicine*, vol. 3, No. 4, pp. 414-420, 1997.

Yakubov, Leonid A., et al., "Mechanism of Oligonucleotide Uptake by Cells: Involvement of Specific Receptors?", *Proc. Natl. Acad. Sci.* USA vol. 86:6454-6458, Sep. 1989.

Politz, Joan C., et al., "Intranuclear Diffusion and Hybridization State of Oligonucleotides Measured by Fluorescence Correlation Spectroscopy in Living Cells", *Proc. Natl. Acad. Sci.*, USA, vol. 95, pp. 6043-6048, May 1998.

Politz, Joan C., et al., "Characterization of Hybridization Between Synthetic Oligodeoxynucleotides and RNA in Living Cells", *Nucleic Acids Research*, vol. 23, No. 24, 1995.

Whitesell, Luke, et al., "Stability, Clearance, and Disposition of Intraventricularly Administered Oligodeoxynucleotides: Implications for Therapeutic Application Within the Central Nervous System", *Proc. Natl. Acad. Sci.*, USA, vol. 90:4665-4669, May 1993.

International Search Report mailed Feb. 22, 2000 from corresponding International Application No. PCT/US99/26128, filed Nov. 5, 1999.

* cited by examiner

TREATMENT OF PARKINSON'S DISEASE WITH OLIGONUCLEOTIDES

This application is a continuation of U.S. application Ser. No. 09/435,249, filed Nov. 5, 1999, abandoned, which claims the benefit of U.S. provisional application Ser. No. 60/107,191, filed Nov. 5, 1998. The full disclosure of each of the above cited applications is incorporated herein by reference.

FIELD OF THE INVENTION

The present invention generally relates to the field of genetic therapy and a method of treatment of Parkinson's disease, and more particularly to the use of antisense oligonucleotides or triplex oligonucleotides introduced into specific brain structures to decrease the function of brain circuits known to be overactive in the Parkinsonian brain.

BACKGROUND OF THE INVENTION

Certain aberrations in the neurochemical circuitry of the brain's basal ganglia are known to result in Parkinson's disease. When dopamine neurons die (the primary pathology in Parkinson's disease), the loss of dopamine to the striatum (caudate nucleus and putamen) sets into motion a series of changes in the neural activity of other brain nuclei located downstream from the striatum. FIG. 1 shows the normal neurochemical circuitry of the brain's basal ganglia.

Current neurosurgical approaches to this problem include either destroying the internal globus pallidus (GPi) by pallidotomy or implanting electrodes for electrical stimulation of this region of the brain. There are major disadvantages to these current neurosurgical approaches. Pallidotomy is permanent; can have serious side effects depending on the precision of the lesion; and can result in dementia and other problems due to destruction of fibers of passage going through the GPi en route to other structures. Electrical stimulation procedures require implantation of electrodes in the brain and a control box under the skin. Over time, a tissue reaction could occur, thereby rendering electrodes useless or dysfunctional. Moreover, chronic electrical stimulation can damage tissue, and epileptic foci kindling may develop as a result of chronic electrical stimulation.

Traditional pharmacotherapies also have serious drawbacks in that the neurochemicals that need to be down-regulated in target structures are ubiquitous in the brain. Systemic administration of inhibitors of these neurochemicals can cause seizures, psychosis, coma, and even death.

The current invention has a number of novel features which represent improvements over the current treatments for Parkinson's disease. In the present invention, molecular neurosurgery is utilized. This approach, through the use of specific antisense or triplex oligonucleotides obviates the problems presented by conventional neurosurgical and pharmacotherapeutic approaches. Via the molecular neurosurgery described more fully below, the current invention selectively alters the functional status of specific groups of neurons without interfering with the functioning of other nearby neurons. This selective approach is made possible by targeting the application of the oligonucleotides to specific neurochemicals in specific neural structures. More precisely, selective targeting occurs by introducing antisense or triplex expression vectors to provide more long-term changes in gene expression. In this way, the result is selective inhibition of the abnormal functioning of certain neural circuits in the Parkinsonian brain without interfering with the normal functioning of these neurochemicals in the rest of the brain. Additionally, by altering the concentration or sequence of the oligonucleotides, the invention makes it possible to titrate the degree to which abnormal activity is inhibited in the target circuits. This ability to titrate further ensures that the treatment only interferes with abnormal functions and does not cause undesirable side effects.

The current invention uses a molecular biological method of treating Parkinson's disease. The antisense oligonucleotides of the present invention are short sequences of phosphorothioate nucleotides, designed in the laboratory. These oligonucleotides block the translation of messenger RNA (mRNA) into protein at the ribosome. (FIG. 2).

Another way to prevent or decrease the expression of deleterious genes is to block transcription of DNA. This approach is also utilized in the present invention. Oligonucleotides, designed in the laboratory, form triplex structures and block the transcription site on target DNAs.

Antisense or triplex oligonucleotides are targeted to the internal globus pallidus and/or substantia nigra pars reticulata (SNr) where the expression of glutamic acid decarboxylase ($GAD_{67}$, $GAD_{65}$, or a combination of the two isoforms) is downregulated; Glutamic acid decarboxylase (in the form of $GAD_{67}$, $GAD_{65}$, or a combination of the two isoforms) is the synthesizing enzyme for the production of the inhibitory neurotransmitter gamma aminobutyric acid (GABA). As a result of glutamic acid decarboxylase downregulation, a decrease occurs in the abnormally high output of GABA by the GPi and the SNr, and the symptoms of Parkinson's disease are ameliorated.

Other targets for the antisense or triplex oligonucleotide treatment of the present invention are the glutamate receptors on neurons in the GPi and the SNr. Decreased expression of these receptors blunts the response of these neurons to increased levels of glutamate released by projections from the subthalamic nucleus (STN) to the GPi and the SNr. (FIG. 3). Another potential target for the antisense or triplex oligonucleotide treatment of the present invention are GABA receptors on neurons in the thalamic motor nuclei that receive excess inhibitory inputs from the GPi and the SNr.

Overall, the present invention is a treatment for Parkinson's disease, which is carried out by administering antisense oligonuculeotides directed to the transcripts encoding the synthesizing enzyme GAD, thereby leading to a highly selective blockade of GABA. Although the actions of the antisense are selective, they will be relatively short-lived. According to the literature, systems return to normal within a few days after cessation of treatment with antisense oligonuculeotides. Typically, in order to demonstrate an effect on protein production, antisense oligonucleotides need to be administered repeatedly or by continuous infusion. As a result, the present invention employs RNA expression vectors. These eucaryotic expression vectors producing RNA antisense to $GAD_{65}$ or $GAD_{67}$ are injected into the desired brain region to transfect neurons so that when the cells receive a signal to produce GABA, the antisense would be activated and GABA is not produced.

SUMMARY OF THE INVENTION

Accordingly, it is an object of the present invention to provide a method of treating Parkinson's disease in a mammal, comprising administering a therapeutically effective amount of antisense oligonucleotide to the substantia nigra pars reticulata for the downregulation of glutamic acid decarboxylase.

It is a further object of the present invention to provide a method of treating Parkinson's disease in a mammal, comprising administering a therapeutically effective amount of antisense oligonucleotide to the substantia nigra pars reticulata for the downregulation of glutamic acid decarboxylase, wherein the isoform of said glutamic acid decarboxylase is $GAD_{65}$.

It is a further object of the present invention to provide a method of treating Parkinson's disease in a mammal, comprising administering a therapeutically effective amount of antisense oligonucleotide to the substantia nigra pars reticulata for the downregulation of glutamic acid decarboxylase, wherein the isoform of said glutamic acid decarboxylase is $GAD_{67}$.

It is a further object of the present invention to provide a method of treating Parkinson's disease in a mammal, comprising administering a therapeutically effective amount of antisense oligonucleotide to the substantia nigra pars reticulata for the downregulation of glutamic acid decarboxylase, wherein the isoform of said glutamic acid decarboxylase is a combination of $GAD_{67}$ and $GAD_{65}$.

It is another object of the present invention to provide a method of treating Parkinson's disease in a mammal, comprising administering a therapeutically effective amount of triplex oligonucleotide to the substantia nigra pars reticulata for the downregulation of glutamic acid decarboxylase.

It is a further object of the present invention to provide a method of treating Parkinson's disease in a mammal, comprising administering a therapeutically effective amount of a triplex oligonucleotide to the substantia nigra pars reticulata for the downregulation of glutamic acid decarboxylase, wherein the isoform of said glutamic acid decarboxylase is $GAD_{65}$.

It is a further object of the present invention to provide a method of treating Parkinson's disease in a mammal, comprising administering a therapeutically effective amount of a triplex oligonucleotide to the substantia nigra pars reticulata for the downregulation of glutamic acid decarboxylase, wherein the isoform of said glutamic acid decarboxylase is $GAD_{67}$.

It is a further object of the present invention to provide a method of treating Parkinson's disease in a mammal, comprising administering a therapeutically effective amount of a triplex oligonucleotide to the substantia nigra pars reticulata for the downregulation of glutamic acid decarboxylase, wherein the isoform of said glutamic acid decarboxylase is a combination of $GAD_{67}$ and $GAD_{65}$.

It is an object of the present invention to provide a method of treating Parkinson's disease in a mammal, comprising administering a therapeutically effective amount of antisense oligonucleotide to the internal globus pallidus for the downregulation of glutamic acid decarboxylase.

It is a further object of the present invention to provide a method of treating Parkinson's disease in a mammal, comprising administering a therapeutically effective amount of antisense oligonucleotide to the internal globus pallidus for the downregulation of glutamic acid decarboxylase, wherein the isoform of said glutamic acid decarboxylase is $GAD_{65}$.

It is a further object of the present invention to provide a method of treating Parkinson's disease in a mammal, comprising administering a therapeutically effective amount of antisense oligonucleotide to the internal globus pallidus for the downregulation of glutamic acid decarboxylase, wherein the isoform of said glutamic acid decarboxylase is $GAD_{67}$.

It is a further object of the present invention to provide a method of treating Parkinson's disease in a mammal, comprising administering a therapeutically effective amount of antisense oligonucleotide to the internal globus pallidus for the downregulation of glutamic acid decarboxylase, wherein the isoform of said glutamic acid decarboxylase is a combination of $GAD_{67}$ and $GAD_{65}$.

It is another object of the present invention to provide a method of treating Parkinson's disease in a mammal, comprising administering a therapeutically effective amount of triplex oligonucleotide to the internal globus pallidus for the downregulation of glutamic acid decarboxylase.

It is a further object of the present invention to provide a method of treating Parkinson's disease in a mammal, comprising administering a therapeutically effective amount of a triplex oligonucleotide to the internal globus pallidus for the downregulation of glutamic acid decarboxylase, wherein the isoform of said glutamic acid decarboxylase is $GAD_{65}$.

It is a further object of the present invention to provide a method of treating Parkinson's disease in a mammal, comprising administering a therapeutically effective amount of a triplex oligonucleotide to the internal globus pallidus for the downregulation of glutamic acid decarboxylase, wherein the isoform of said glutamic acid decarboxylase is $GAD_{67}$.

It is a further object of the present invention to provide a method of treating Parkinson's disease in a mammal, comprising administering a therapeutically effective amount of a triplex oligonucleotide to the internal globus pallidus for the downregulation of glutamic acid decarboxylase, wherein the isoform of said glutamic acid decarboxylase is a combination of $GAD_{67}$ and $GAD_{65}$.

It is another object of the present invention to provide a method of treating Parkinson's disease in a mammal, comprising administering a therapeutically effective amount of antisense oligonucleotide to the substantia nigra pars reticulata for the downregulation of glutamate receptors.

It is another object of the present invention to provide a method of treating Parkinson's disease in a mammal, comprising administering a therapeutically effective amount of triplex oligonucleotide to the substantia nigra pars reticulata for the downregulation of glutamate receptors.

It is another object of the present invention to provide a method of treating Parkinson's disease in a mammal, comprising administering a therapeutically effective amount of antisense oligonucleotide to the internal globus pallidus for the downregulation of glutamate receptors.

It is another object of the present invention to provide a method of treating Parkinson's disease in a mammal, comprising administering a therapeutically effective amount of triplex oligonucleotide to the internal globus pallidus for the downregulation of glutamate receptors.

It is another object of the present invention to provide a method of treating Parkinson's disease in a mammal, comprising administering a therapeutically effective amount of antisense oligonucleotide to the thalamic motor nuclei for the downregulation of GABA receptors.

It is another object of the present invention to provide a method of treating Parkinson's disease in a mammal, comprising administering a therapeutically effective amount of triplex oligonucleotide to the thalamic motor nuclei for the downregulation of GABA receptors.

DETAILED DESCRIPTION

Oligodeoxynucleotides

Figure 1:
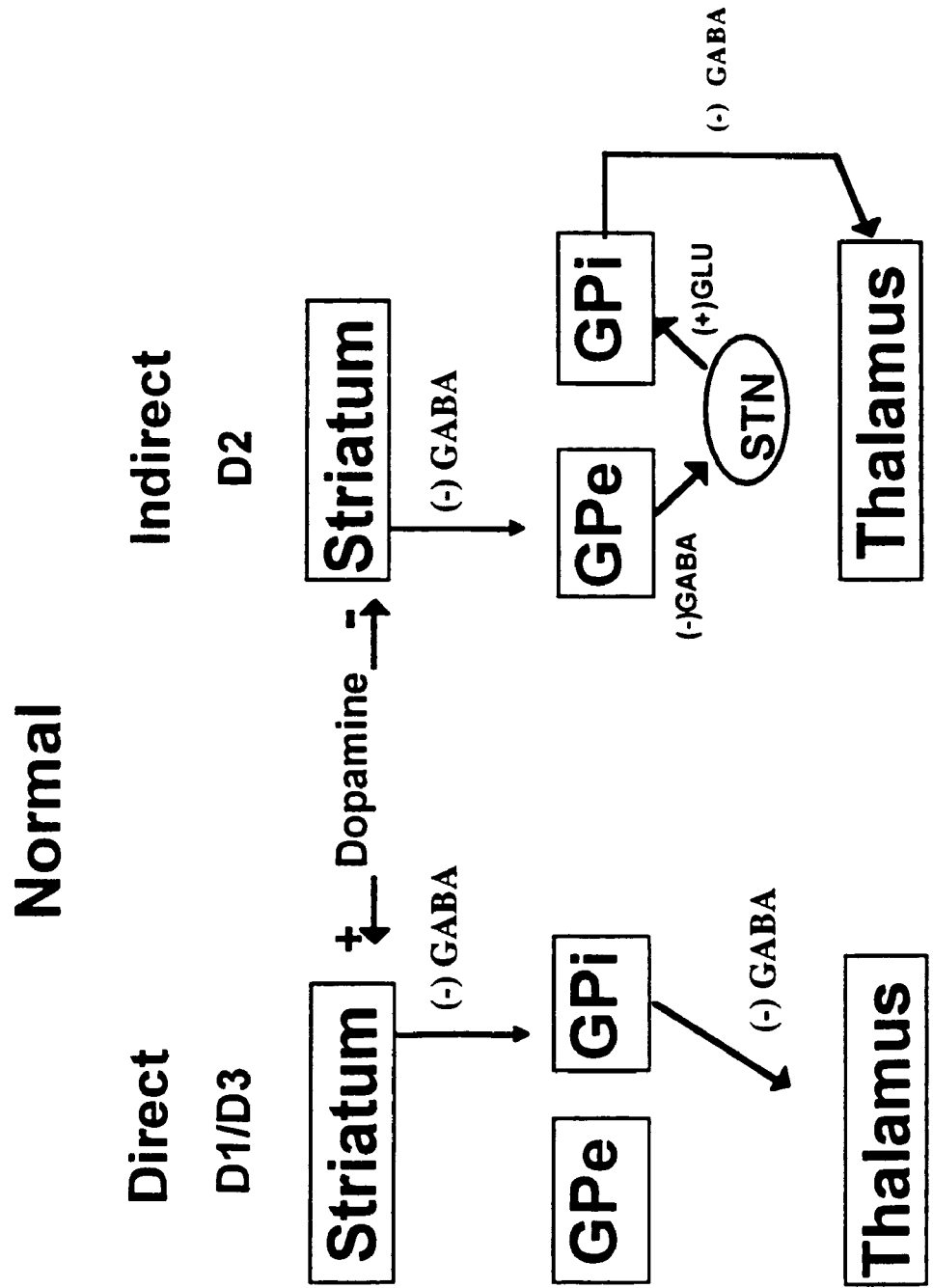
FIG. 1. A diagram of normal direct and indirect dopamine effects in the neurochemical circuitry of the brain's basal ganglia.
Figure 2:
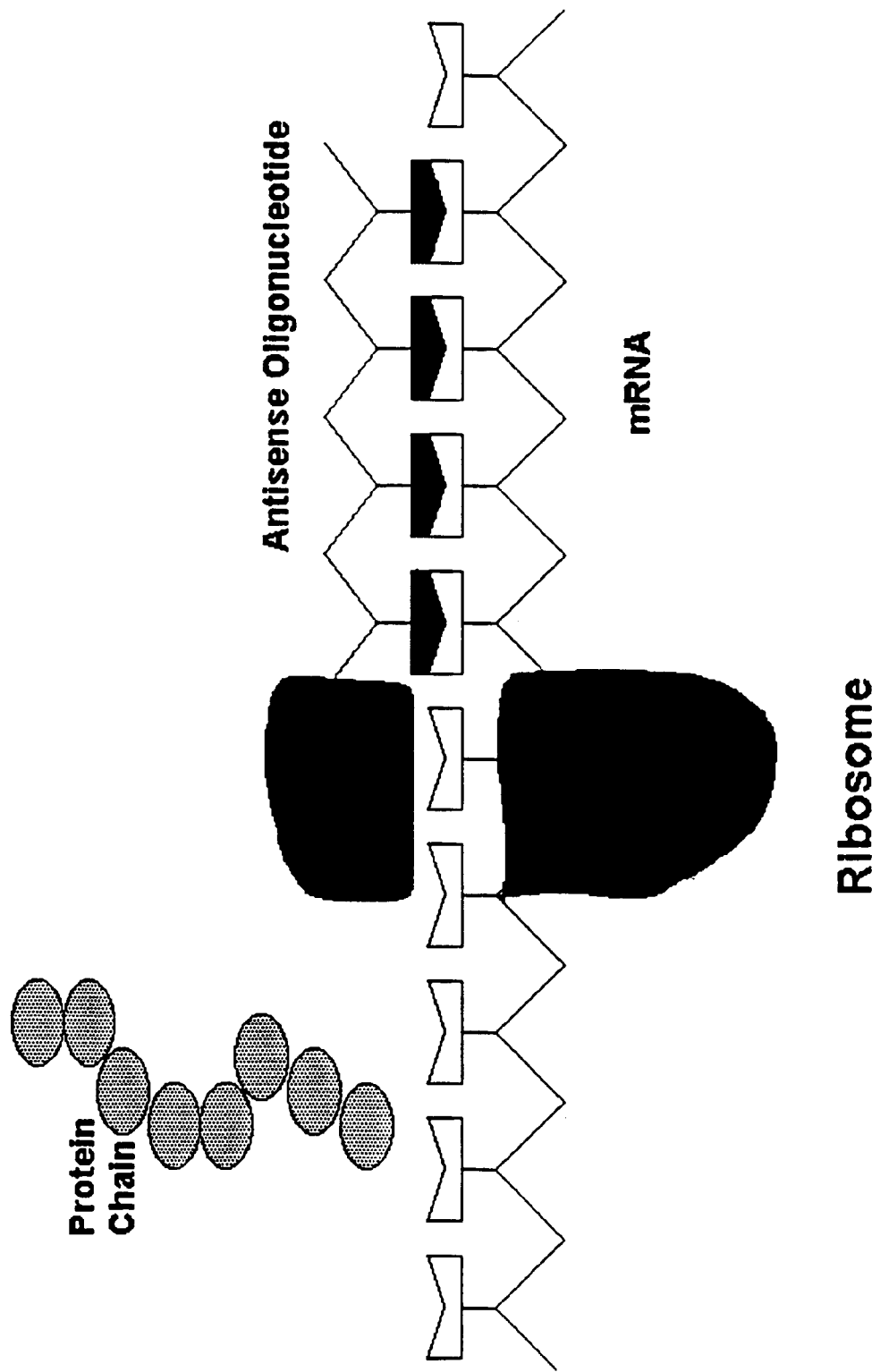
FIG. 2. A schematic representation of how antisense oligonucelotide can block protein translation by hybridizing to the complementary glutamic acid decarboxylase mRNA. The antisense oligonucleotide hybridizes to the complementary target mRNA and causes a block of protein tranlation.
Figure 3:
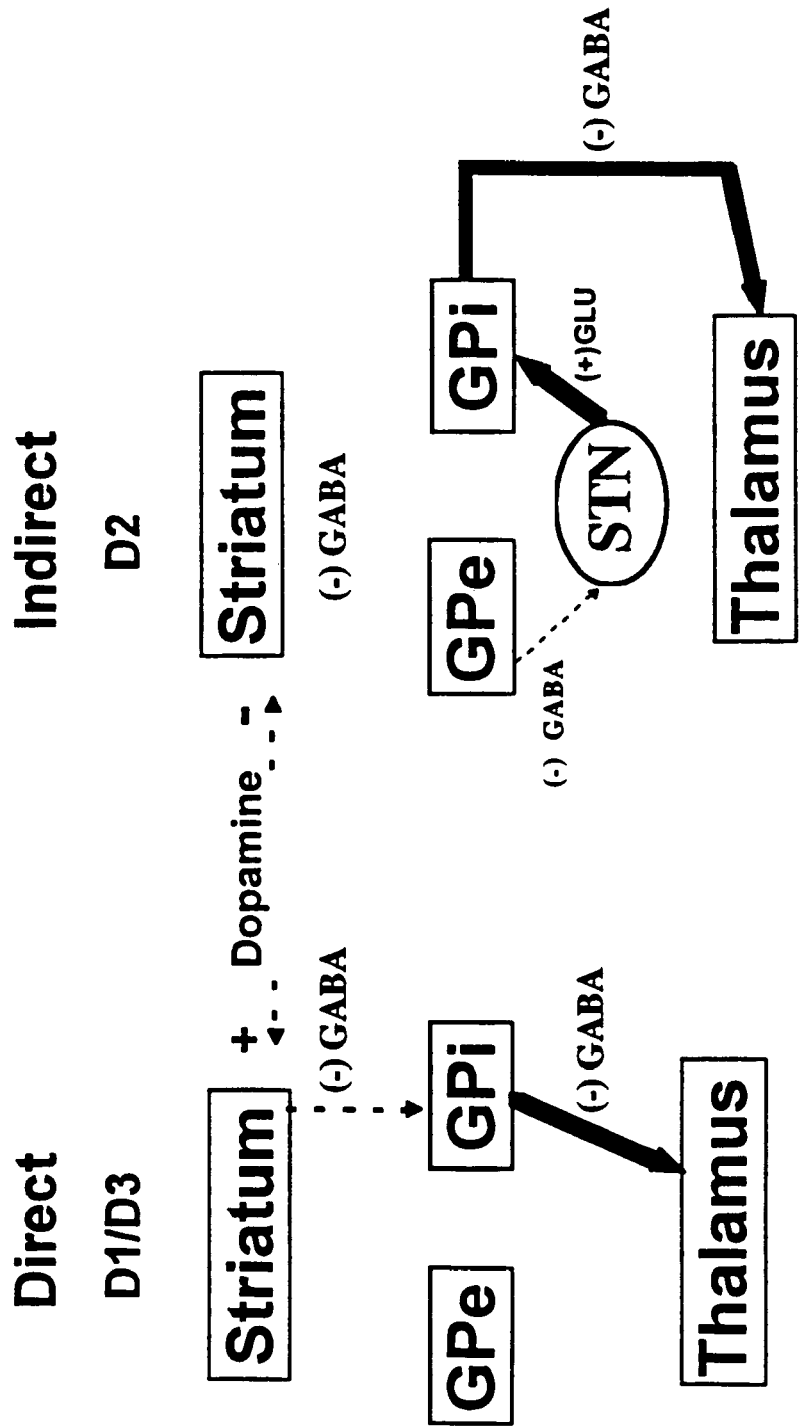
FIG. 3. A diagram of the aberrations of the neurochemical circuitry of the brain's basal ganglia when dopamine loss occurs in the Parkinsonian brain.

Phosphorthioate oligonucleotides were synthesized by Biosynthesis Inc., Lewisville, Tex. Since initial feasibility studies were conducted in rats, the first produced antisense oligonucleotides were directed against rat GAD sequences. The sequence used to generate rat $GAD_{67}$ antisense was 5'TGGAAGATGCCATCAGCTCGG3' (SEQ ID NO:1). The sequence used to generate rat $GAD_{65}$ antisense was 5'CCGGAGATGCCATGGGTTCTG3' (SEQ ID NO:2). The sequence used to generate human $GAD_{65}$ is 5'CCGGAGATGCCATCGGCTTTG3' (SEQ ID NO:3). The sequence used to generate human $GAD_{67}$ is 5'TCGAAGACGCCATCAGCTCGG3' (SEQ ID NO:4). The antisense sequence used for the monkey (Saimiri sciureus) studies was the $GAD_{67}$: 5'-GAAGATGGGGTCGAAGACGC-3' (SEQ ID NO:5). SEQ ID No:5 is an antisense molecule complementary to the 20 nucleotides starting with the fourth base downstream of the translation initiation site in the gene encoding human GAD67. The control oligonucleotide for the monkey and rat $GAD_{67}$ studies was a scrambled nucleotide sequence of the monkey studies $GAD_{67}$ antisense sequence: 5'-TAGGAGCAGACTGAGAGGGCG-3' (SEQ ID NO:6).

These sequences were obtained by searching Genbank for the appropriate gene name. These sequences were analyzed using an open reading frame finder program at the National Center for Biotechnology Information World Wide Web site. The initiation of translation site was found and a 21 base antisense molecule complementary to the region spanning 8 bases 5' to 13 bases 3' (−8 to +13) to the initiation triplet was selected. These 21 base oligonucleotides were analyzed for cross reactivity with other genes using the NCBI BLAST server.

The results of this search indicated that the oligos were only homologous with the genes they were directed against. Based on the BLAST algorithm, rat antisense molecules could react with GAD RNA of rat (Rattus norvegicus) and mouse (mus musculus). Further manual analysis of $GAD_{67}$ revealed a 90.5% sequence identity between rat, pig (Sus scrofa) and human (Homo sapien) at the mRNA level surrounding the translation initiation site. Manual analysis of $GAD_{65}$ sequences indicate 85.7% identify with human $GAD_{65}$ in the region surrounding the initiation of translation site. Based on the BLAST algorithm, human $GAD_{65}$ antisense molecules could react with human GAD-2 mRNA (a glutamate decarboxylase gene found in the human pancreas) and human $GAD_{65}$. The human $GAD_{67}$ antisense molecule could react with human $GAD_{67}$ (both in the brain and pancreas isoforms) and $GAD_{67}$ from both pig and cat (Felis cactus).

The rat $GAD_{67}$ antisense (SEQ ID NO:1) is composed of 23.8% adenosine, 23.8% cytosine, 33.3% guanine, and 19.0% thymine. The rat $GAD_{65}$ antisense (SEQ ID NO:2) is composed of 14.3% adenosine, 23.8% cytosine, 38.1% guanine, and 23.8% thymine. The human $GAD_{67}$ (SEQ ID NO:4) is composed of 23.8% adenosine, 33.3% cytosine, 28.6% guanine, and 14.3% thymine. The human $GAD_{65}$ (SEQ ID NO:3) is composed of 14.3% adenosine, 28.6% cytosine, 33.3% guanine, and 23.8% thymine. A missense molecule to be used in control experiments was designed by scrambling the base order of the antisense molecule. This control oligonucleotide for the $GAD_{67}$ studies was a scrambled nucleotide sequence of the monkey (Saimiri sciureus) studies $GAD_{67}$ antisense sequence: 5'-TAGGAGCAGACTGAGAGGGCG-3' (SEQ ID NO:6). The missense has the same percentages of each nucleotide as the antisense but the sequence has been changed. The missense oligonucleotides were analyzed using the NCBI BLAST server. The results of this analysis indicate that the missense molecules have no detectable homology with any known genes.

The antisense oligonucleotide was dissolved in sterile artificial cerebrospinal fluid (124 mM NaCl, 1 mM KCl, 2.4 mM $CaCl_2$, 26 mM $NaHCO_3$, 1.24 mM $NaH_2PO_4$, 2 mM D-glucose, and 1.3 mM $MgSO_4$) to a final concentration of 43.1 µM. This resulted in an infusion of 21.5 µM/hr over a 2 week period.

Animals

Initial studies have been conducted in adult male Sprague-Dawley rats (226-250 g). Animals were anesthetized with sodium pentobarbital and placed in standard stereotaxic frame. Animals were given unilateral lesions of the nigrostriatal dopamine system using the neurotoxin 6-hydroxdopamine-hydrobromide (6-OHDA-HBr). Two injections of 8 mM 6-OHDA-HBr in 0.9% NaCl containing 1.4 mM ascorbic acid were made into the substantial nigra pars compacta (SNc) on one side of the brain. One injection was placed into the medial SNc and the other into the lateral SNc. Four weeks after lesioning, rats were assessed for the degree of rotational asymmetry after injection with the dopamine agonist apomorphine. Apomorphine-induced rotations in a direction away from the side of lesion is a standard measure of experimentally-induced parkinsonism in rats. The ability of a drug to attenuate apomorphine-induced rotations is an accepted measure of anti-Parkinson efficacy. The number of complete 360 degree rotations was counted in 5-minute epochs over a total observation period of 1 hour. Rats rotating an average of 5 times per minute or more are considered to have at least 90% lesion to the nigrostriatal dopamine system. Animals with fewer rotations have lesser degrees of dopamine system damage.

Antisense Treatment

Once animals were shown to have lesion-induced rotations in response to apomorphine administration, they were randomly assigned to receive antisense treatment or sham infusions. The antisense was delivered via Alzet model 2002 mini asmotic pumps (Alza Corp. Palo Alto, Calif.), and a 32 gauge custom cannula (9.5 mm below pedestal) which were made by Plastics One Inc. (Roanoke, Va.). These pumps are designed to pump at a rate of approximately 0.5 µL/hr for 14 days. This results in a total antisense infusion of 7,241 pmols. The pumps and cannula were prepared according to manufacturer instructions. Briefly, the pumps were filled under sterile conditions with 250 microliters of either rat $GAD_{67}$ antisense (SEQ ID NO:1) or control or missense (SEQ ID NO:6) vehicle solution. A flow moderator, cannula for brain infusion and 4 mm of connector tubing were connected and attached to the pump. The pump assembly was then primed over night at 37° C. in sterile saline. The pumps were implanted into animals the following day.

For pump implantation, rats were anesthetized with sodium pentobarbital and placed in a standard stereotaxic device on a homeothermic blanket. Core temperature was maintained at 37° C. In some animals the brain infusion cannula was implanted just above the entopeduncular nucleus (the rodent analog of the Gpi, 2.3 mm behind bregma, 2.5 mm lateral to the midline and 7.7 mm below the skull surface, according to the atlas of Paxinos and Watson). Other animals had the brain infusion cannula implanted just above the substantia nigra pars reticulate (5.3 mm behind bregma, 2.5 mm lateral to the midline, 8.2 mm below the skull surface, according to the atlas of Paxinos and Watson). These two targets were chosen because they represent the two major output areas of the basal ganglia. Overactivity of GABA-containing neurons in these brain regions are most likely responsible for the expression of Parkinsonian symptoms. The cannulae were secured in place with dental acrylic. All animals had the Alzet pump placed in a subcutaneous pocket located between the scapulae on the back. Scalp wounds were closed with Autoclip wound clips and rats were kept warm until they regained consciousness.

Rats were again tested for apomorphine-induced rotations at 7 and 14 days after osmotic pump implantation. Fifteen to 17 days after pump implantation, animals were killed by decapitation and brains were immediately removed for analysis. Brains were removed and either flash frozen on dry ice for immunohistochemistry or microdissected for HPLC analysis of GABA content.

Additional antisense experiments were carried out whereby a single injection of antisense oligonucleotide was given to nine rats. These nine rats were lesioned with 6-OHDA, as described above. Approximately 3 to 4 weeks after lesioning, rats were tested for apomorphine-induced rotational asymmetry as described above. Once the integrity of the lesion was confirmed by a positive rotation response, animals were implanted with a guide cannula situated in the brain overlying the entopeduncular nucleus. Within weeks of recovery from surgery, rotational asymmetry was assessed again to re-establish a baseline response. Rats were then lightly anesthetized with an isofluorane/oxygen mixture and antisense oligonucleotide to $GAD_{67}$ (SEQ ID NO:1)was slowly infused into the entopeduncular nucleus via an injection cannula inserted through the guide cannula. Each injection contained 250 ng of antisense in 0.5 µl.

Three squirrel monkeys (1 male, 2 female) were used for this pilot study. All animals had gross activity measures recorded while in an observation cage with use of an automated Doppler-based activity monitoring system. Activity measures were first recorded when animals were normal. At least 3 to 5 activity sessions were recorded, each lasting at least 2 to 3 hours. Animals were then made Parkinsonian by administration of several doses of the neurotoxin MPTP (1.5 to 2.5 mg/kg, i.m.). Toxin was administered until animals developed a stable Parkinsonian syndrome. Animals were stably Parkinsonian for a minimum of 6 months prior to antisense treatment. In preparation for antisense administration, animals were implanted with dual cannulae overlying the internal segment of the globus pallidus bilaterally. After surgery, activity measures were recorded once again to insure that there was no shift in baseline activity measures. After at least a week recovery period following surgery, the monkeys were restrained in a primate chair and antisense oligonucleotide was slowing infused into the internal globus pallidus sites via internal cannulae inserted through the implanted guide cannulae.

For each experiment, $GAD_{67}$ (SEQ ID NO:5) oligonucleotide was diluted fresh in sterile artificial cerebrospinal fluid (CSF). A total injection of 500 ng was made, with 250 ng injected into each of the sites on each side of the brain. The injection volume was 1.0 to 2.0 µl. Following administration of antisense, animals were returned to their cages and activity monitoring began 24 to 48 hrs. later and was recorded at various times over the next 2 to 3 wks. After antisense studies were performed, the same procedure was repeated using a missense oligonucleotide that was a scrambled sequence of the antisense oligonucleotide. Studies with the missense oligonucleotide (SEQ ID NO:6) were performed exactly as the antisense studies.

Results

In normal rats implanted with $GAD_{67}$ antisense (SEQ ID NO:1) in the globus pallidus, HPLC analysis showed that a 2 week antisense infusion into the entopeduncular nucleus caused on average 65% reduction in GABA levels when compared with the contralateral untreated hemisphere.

Figure 4:
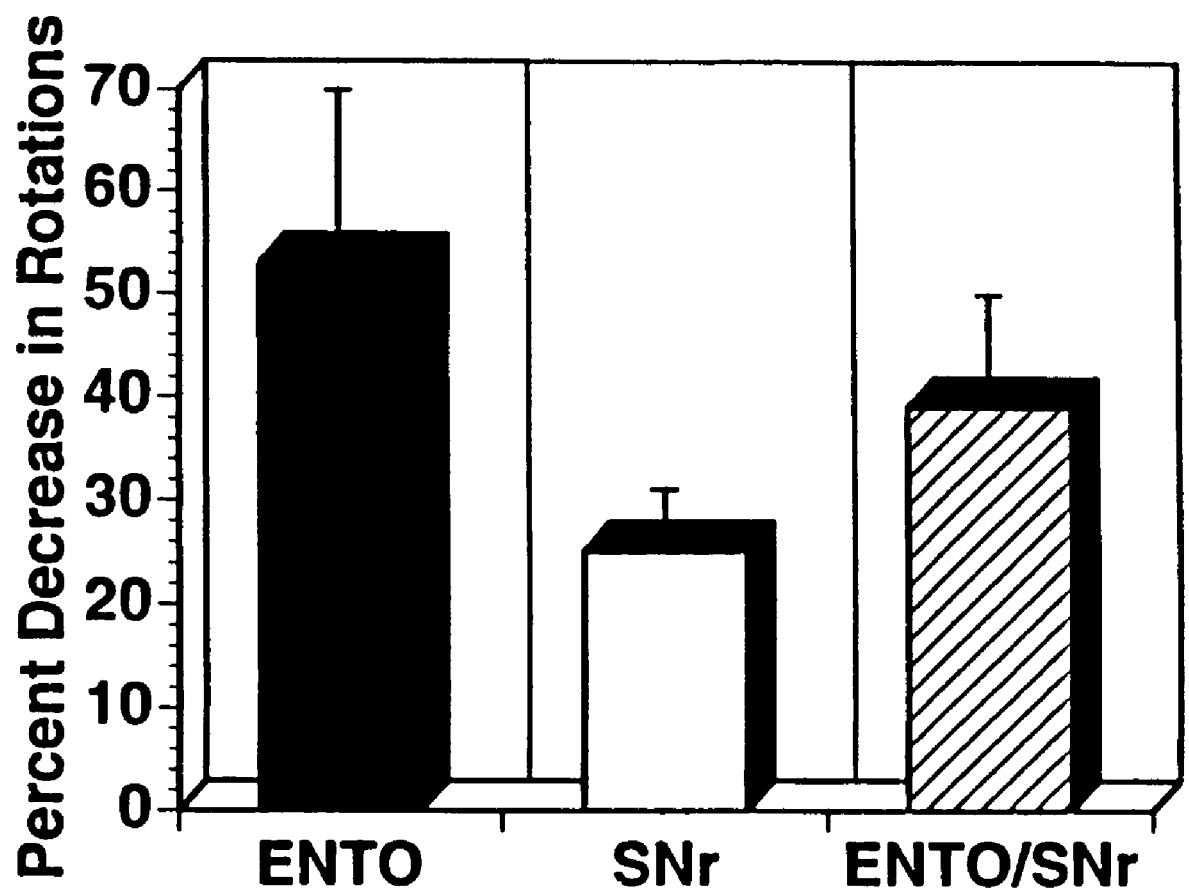
FIG. 4. A bar graph showing the percent reduction in apomorphine-induced rotations of $GAD_{67}$ infused animals with experimentally-induced parkinsonism.
Figure 5:
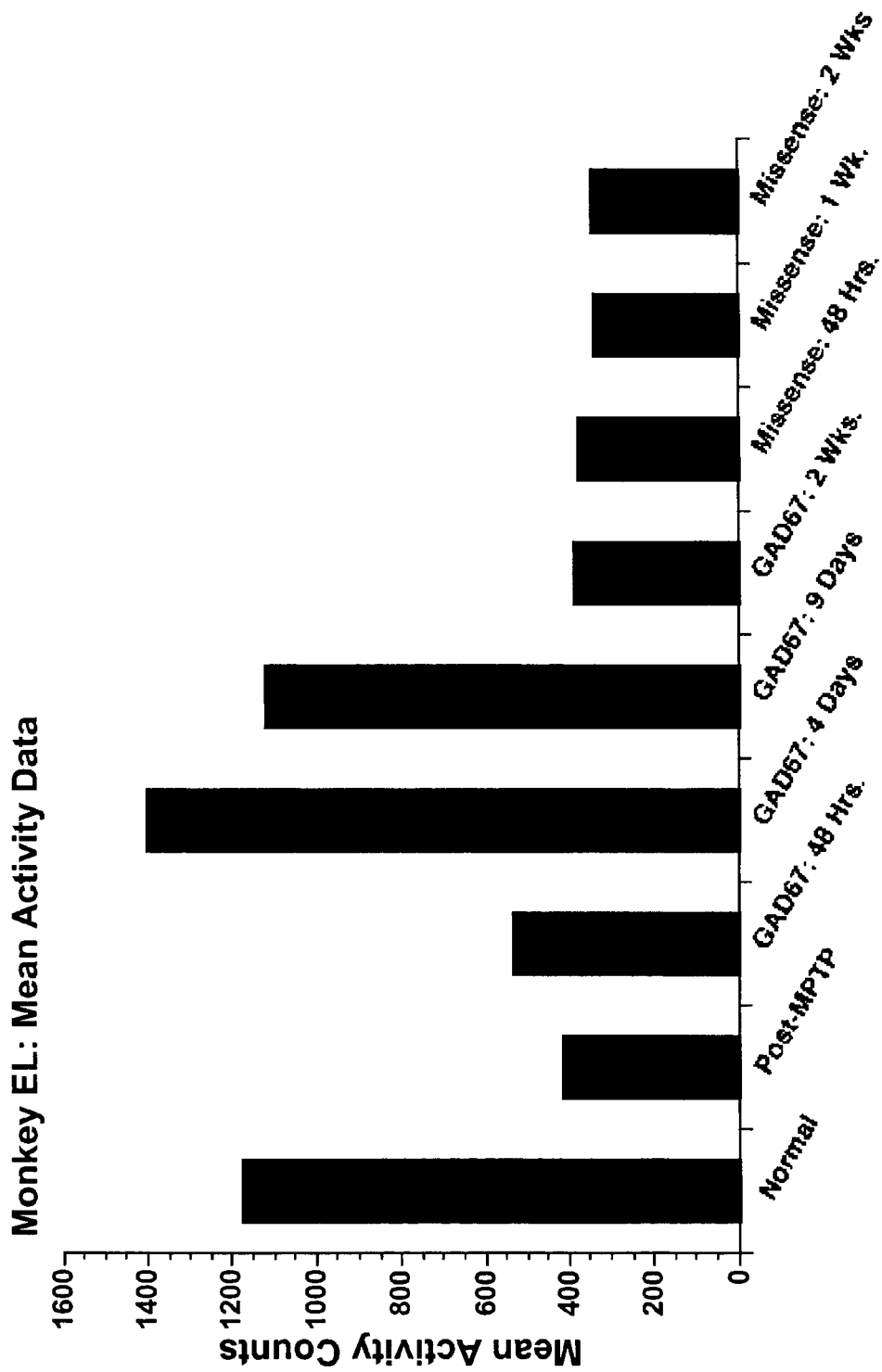
FIG. 5-7. Bar graphs showing the relative changes in activity before and after treatment with $GAD_{67}$ infused monkeys with experimentally-induced parkinsonism.
Figure 6:
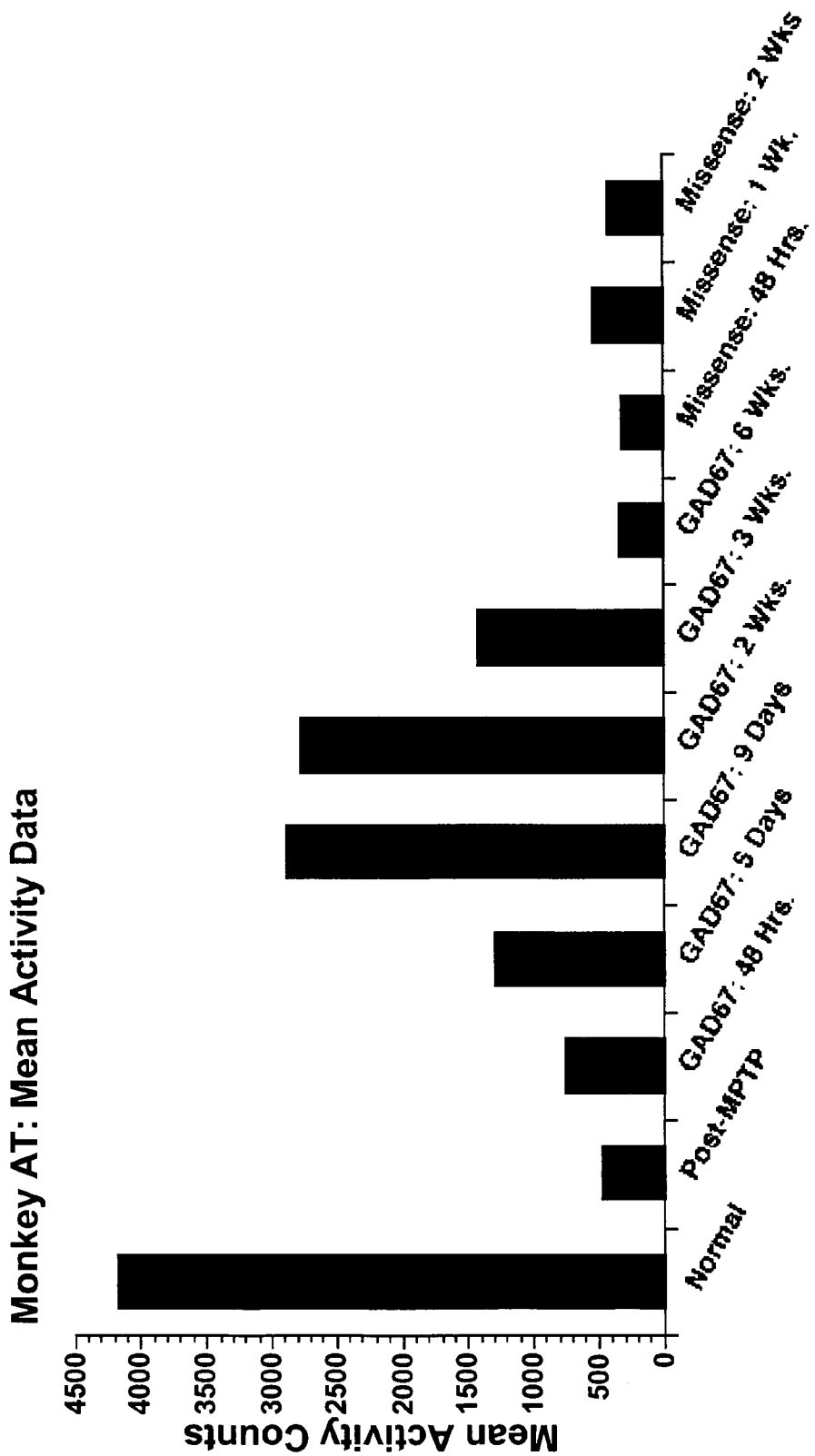
Figure 7:
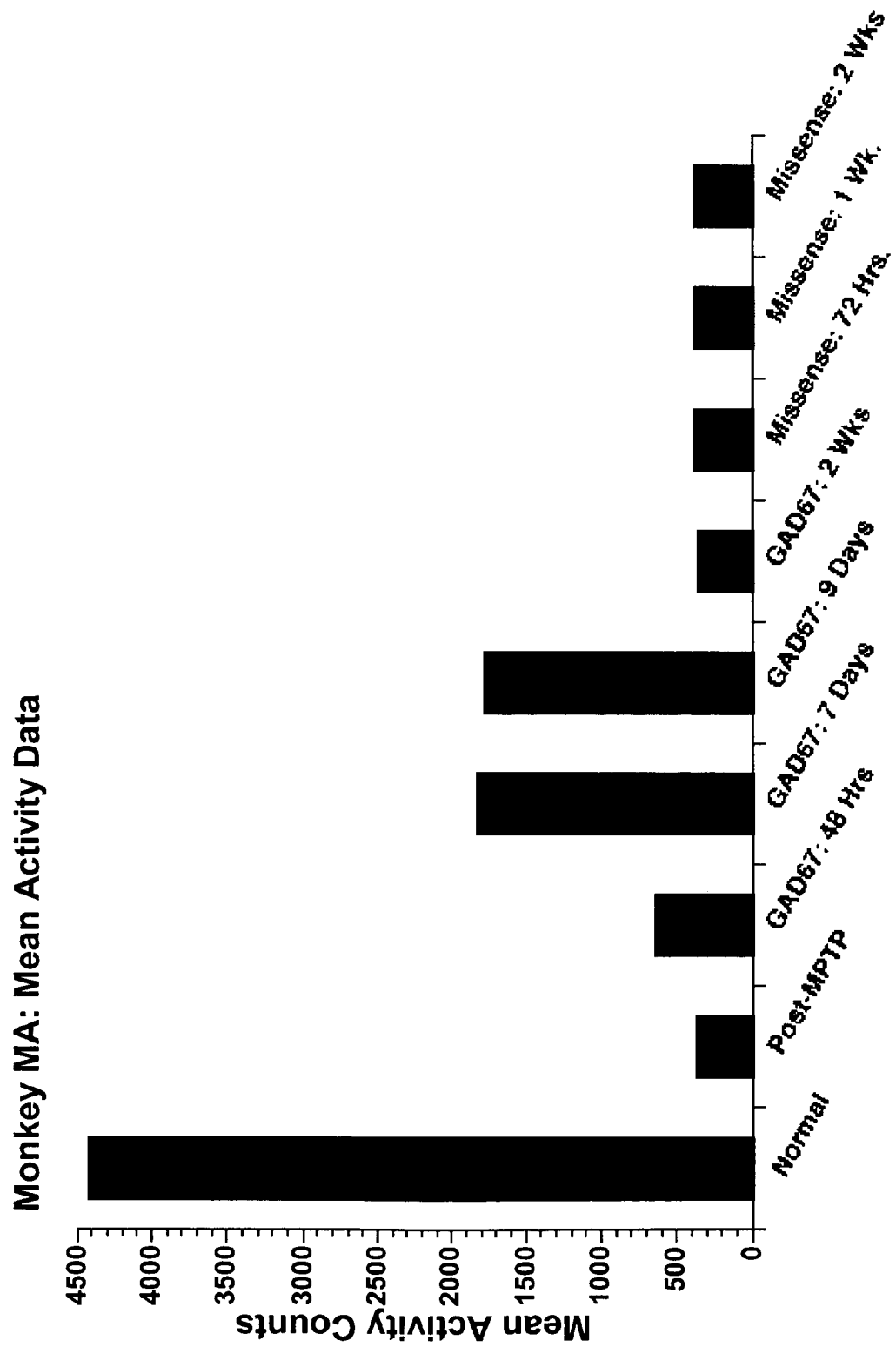

Rats that had $GAD_{67}$ antisense (SEQ ID NO:1) infused above the entopeduncular nucleus had the number of apomorphine-induced rotations reduced by an average of 52%. Rats that had the $GAD_{67}$ antisense (SEQ ID NO:1) infused above the substantia nigra pars reticulata (SNr) had the number of apomorphine-induced rotations reduced by an average of 31%. The combined improvement in rotational asymmetry from both groups of animals is approximately 39%. FIG. 4 is a graphical representation of these results. A change in the surgical coordinates may improve the response to SNr antisense infusion. Simultaneous infusions into both structures may also improve the response. In comparison, rats that received sham infusion showed an increase in apomorphine-induced rotations of 23% over the same time period.

Rats that had received the single injection method, apomorphine-induced rotations were reduced by an average of 34% when measured 24 hours after infusion. By 6 days after infusion, rotations were increased 5% above pre-antisense levels. The same rats received infusion of the scrambled oligonucleotide (SEQ ID NO:6) and these animals showed 25% and 38% increases in apomorphine-induced rotations 24 hours and 6 days, respectively, after control infusion.

These data demonstrate the feasibility and efficacy of this treatment as a means to reduce Parkinsonian symptomatology in a model commonly accepted for screening efficacy of potential new anti-Parkinson therapeutics.

The results of the monkey pilot study revealed that although the time courses and magnitudes of the effect differed slightly across the 3 animals, all animals showed an increase in spontaneous activity (a lessening of akinesia and bradykinesia) following antisense (SEQ ID NO:5) treatment but not following missense oligonucleotide (SEQ ID NO:6) treatment. Individual animal differences could have been due to slight differences in placement of the injection cannulae and individual differences in the degree of Parkinsonism and levels of spontaneous activity. Nontheless, these non-human primate studies present proof of principle that the therapy has potential beneficial effects on the major symptoms of Parkinson's disease.

What is claimed is:

1. A method of treating Parkinson's disease in a mammal, comprising administering a therapeutically effective amount of antisense oligonucleotide comprising SEQ ID NO:1, SEQ ID NO:2, SEQ ID NO:3, SEQ ID NO:4 or SEQ ID NO:5 to the substantia nigra pars reticulata via a cannula for the down-regulation of glutamic acid decarboxylase.

2. The method of claim 1 wherein the glutamic acid decarboxylase comprises the glutamic acid decarboxylase isoform $GAD_{65}$.

3. The method of claim 1 wherein the glutamic acid decarboxylase comprises the glutamic acid decarboxylase isoform $GAD_{67}$.

4. The method of claim 1 wherein the glutamic acid decarboxylase comprises a combination of the glutamic acid decarboxylase isoforms $GAD_{65}$ and $GAD_{67}$.

5. The method of claim 1, wherein the oligonucleotide comprises phosphorothioate linkages.

6. A method of treating Parkinson's disease in a mammal, comprising administering a therapeutically effective amount of antisense oligonucleotide comprising SEQ ID NO:1, SEQ ID NO:2, SEQ ID NO:3, SEQ ID NO:4 or SEQ ID NO:5 to the internal globus pallidus or entopeduncular nucleus via a cannula for the downregulation of glutamic acid decarboxylase.

7. The method of claim 6 wherein the glutamic acid decarboxylase comprises the glutamic acid decarboxylase isoform $GAD_{65}$.

8. The method of claim 6 wherein the glutamic acid decarboxylase comprises the glutamic acid decarboxylase isoform $GAD_{67}$.

9. The method of claim 6 wherein the glutamic acid decarboxylase comprises a combination of the glutamic acid decarboxylase isoforms $GAD_{65}$ and $GAD_{67}$.

10. The method of claim 6, wherein the oligonucleotide comprises phosphorothioate linkages.

11. A method of downregulating glutamic acid decarboxylase in a mammal in vivo, comprising administering an antisense oligonucleotide directed to an initiation codon of glutamic acid decarboxylase mRNA to the substantia nigra pars reticulata or internal globus pallidus or entopeduncular nucleus via a cannula, wherein said antisense oligonucleotide comprises SEQ ID NO:1, SEQ ID NO:2, SEQ ID NO:3, SEQ ID NO:4 or SEQ ID NO:5.

12. The method of claim 11, wherein the oligonucleotide comprises phosphorothioate linkages.

13. The method of claim 11, wherein said administering is to both the substantia nigra pars reticulata and internal globus pallidus or entopeduncular nucleus.

14. The method of claim 1, wherein said administering is to both the substantia nigra pars reticulata and internal globus pallidus or entopeduncular nucleus.

15. A method of treating Parkinson's disease in a mammal, comprising administering a therapeutically effective amount of a combination of antisense oligonucleotides comprising SEQ ID NO:1 and SEQ ID NO:2, SEQ ID NO:3 and SEQ ID NO:4, or SEQ ID NO:3 and SEQ ID NO:5, to the substantia nigra pars reticulata via a cannula for the downregulation of glutamic acid decarboxylase.

16. A method of treating Parkinson's disease in a mammal, comprising administering a therapeutically effective amount of a combination of antisense oligonucleotides comprising SEQ ID NO:1 and SEQ ID NO:2, SEQ ID NO:3 and SEQ ID NO:4, or SEQ ID NO:3 and SEQ ID NO:5, to the internal globus pallidus or entopeduncular nucleus via a cannula for the downregulation of glutamic acid decarboxylase.

17. The method of claim 1, wherein the antisense oligonucleotide comprises SEQ ID NO:1, SEQ ID NO:2 or SEQ ID NO:5.

18. The method of claim 6, wherein the antisense oligonucleotide comprises SEQ ID NO:1, SEQ ID NO:2 or SEQ ID NO:5.

19. The method of claim 11, wherein the antisense oligonucleotide comprises SEQ ID NO:1, SEQ ID NO:2 or SEQ ID NO:5.

20. The method of claim 16, wherein the combination of antisense oligonucleotides comprises SEQ ID NO:1 and SEQ ID NO:2.

21. The method of claim 1, wherein the mammal is human and the antisense oligonucleotide comprises SEQ ID NO:3 or SEQ ID NO:4.

22. The method of claim 6, wherein the mammal is human and the antisense oligonucleotide comprises SEQ ID NO:3 or SEQ ID NO:4.

23. The method of claim 11, wherein the mammal is human and the antisense oligonucleotide comprises SEQ ID NO:3 or SEQ ID NO:4.

24. The method of claim 16, wherein the mammal is human and the combination of antisense oligonucleotides comprises SEQ ID NO:3 and SEQ ID NO:4.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Rattus norvegicus

<400> SEQUENCE: 1
tggaagatgc catcagctcg g                                          21

<210> SEQ ID NO 2
<211> LENGTH: 21
<212> TYPE: DNA
<213> ORGANISM: Rattus norvegicus

<400> SEQUENCE: 2
ccggagatgc catgggttct g                                          21

<210> SEQ ID NO 3
<211> LENGTH: 21
<212> TYPE: DNA
<213> ORGANISM: Homo sapiens

<400> SEQUENCE: 3
ccggagatgc catcggcttt g                                          21

<210> SEQ ID NO 4
<211> LENGTH: 21
<212> TYPE: DNA
<213> ORGANISM: Homo sapiens

<400> SEQUENCE: 4
tcgaagacgc catcagctcg g                                          21

<210> SEQ ID NO 5
<211> LENGTH: 20
<212> TYPE: DNA
<213> ORGANISM: Saimiri sciureus

<400> SEQUENCE: 5
gaagatgggg tcgaagacgc                                            20

<210> SEQ ID NO 6
<211> LENGTH: 21
<212> TYPE: DNA
<213> ORGANISM: Saimiri sciureus

<400> SEQUENCE: 6
taggagcaga ctgagagggc g                                          21
```